United States Patent
Schabbach et al.

(10) Patent No.: US 10,874,588 B2
(45) Date of Patent: Dec. 29, 2020

(54) RESERVOIR FOR LIQUID MEDICAMENT

(71) Applicant: SANOFI-AVENTIS DEUTSCHLAND GMBH, Frankfurt am Main (DE)

(72) Inventors: Michael Schabbach, Frankfurt am Main (DE); Daniel Auernhammer, Frankfurt am Main (DE); Daniel Wagner, Frankfurt am Main (DE); Bernd Kuhn, Frankfurt am (DE); Isabel Klein, Frankfurt am (DE); Pierre Weiss, Schwalbach (DE); Klaus Schepers, Braunfels (DE); Horst Mischo, Trier (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 76 days.

(21) Appl. No.: 15/115,236

(22) PCT Filed: Feb. 11, 2015

(86) PCT No.: PCT/EP2015/052822
§ 371 (c)(1),
(2) Date: Jul. 28, 2016

(87) PCT Pub. No.: WO2015/121276
PCT Pub. Date: Aug. 20, 2015

(65) Prior Publication Data
US 2017/0007500 A1    Jan. 12, 2017

(30) Foreign Application Priority Data
Feb. 12, 2014    (EP) .................................... 14154778

(51) Int. Cl.
*A61J 1/14* (2006.01)
*A61M 5/14* (2006.01)
(Continued)

(52) U.S. Cl.
CPC ............. *A61J 1/1468* (2015.05); *A61J 1/035* (2013.01); *A61J 1/05* (2013.01); *A61J 1/067* (2013.01);
(Continued)

(58) Field of Classification Search
CPC ........ A61M 5/282; A61M 5/002; A61M 5/14; A61J 1/067; A61J 1/1493; A61J 1/2024; A61J 1/1468; A61J 1/035; A61J 1/18
See application file for complete search history.

(56) References Cited

U.S. PATENT DOCUMENTS 2,293,589 A     8/1942  Calvert
3,342,326 A *   9/1967  Zackheim ............... A61J 1/067
                                                 206/438

(Continued)

FOREIGN PATENT DOCUMENTS

CH          328609       3/1958
GB          1539598      1/1979
(Continued)

OTHER PUBLICATIONS

International Search Report and Written Opinion in International Application No. PCT/EP2015/052822, dated May 13, 2015, 9 pages.

(Continued)

*Primary Examiner* — Manuel A Mendez
*Assistant Examiner* — Justin L Zamory
(74) *Attorney, Agent, or Firm* — Fish & Richardson P.C.

(57) ABSTRACT

A reservoir for liquid medicament includes a first boundary portion and a second boundary portion forming at least one cavity to receive the medicament. The first boundary portion is flexible, while the second boundary portion is rigid. At least one of the first and second boundary portions is a transparent boundary portion covered by an opaque cover (Continued)

which is at least partially detachable from the transparent boundary portion.

21 Claims, 4 Drawing Sheets

(51) Int. Cl.
| | | |
|---|---|---|
| | *A61J 1/18* | (2006.01) |
| | *A61J 1/06* | (2006.01) |
| | *A61J 1/03* | (2006.01) |
| | *A61J 1/05* | (2006.01) |
| | *A61M 5/00* | (2006.01) |

(52) U.S. Cl.
CPC ............... *A61J 1/18* (2013.01); *A61M 5/14* (2013.01); *A61M 5/002* (2013.01)

(56) References Cited

U.S. PATENT DOCUMENTS

| | | | | |
|---|---|---|---|---|
| 3,473,524 A | * | 10/1969 | Drewe | A61M 3/00 |
| | | | | 222/215 |
| 4,282,986 A | * | 8/1981 | af Ekenstam | A61M 5/282 |
| | | | | 222/1 |
| 5,019,033 A | * | 5/1991 | Geria | A61M 35/006 |
| | | | | 401/183 |
| 2003/0196914 A1 | | 10/2003 | Tzou et al. | |
| 2009/0118682 A1 | | 5/2009 | Hansen et al. | |
| 2010/0308075 A1 | * | 12/2010 | Herold | B65D 47/265 |
| | | | | 222/1 |

FOREIGN PATENT DOCUMENTS

| | | |
|---|---|---|
| GB | 2254306 | 10/1992 |
| JP | S51-143481 | 3/1976 |
| JP | 2003-250863 | 9/2003 |
| WO | WO 2003/103563 | 12/2003 |
| WO | WO 2009/115467 | 9/2009 |

OTHER PUBLICATIONS

International Preliminary Report on Patentability in International Application No. PCT/EP2015/052822, dated Aug. 16, 2016.

Rote Liste, "50. Hypophysen-, Hypothalamushonnone, andere regulatorische Peptide u. ihre Hemmstoffe," Chapter 50, ed. 2008, 20 pages.

* cited by examiner

RESERVOIR FOR LIQUID MEDICAMENT

CROSS-REFERENCE TO RELATED APPLICATIONS

This application is a U.S. national stage application under 35 USC § 371 of International Application No. PCT/EP2015/052822, filed on Feb. 11, 2015, which claims priority to European Patent Application No. 14154778.6, filed on Feb. 12, 2014, the entire contents of which are incorporated herein by reference.

TECHNICAL FIELD

The present disclosure relates to the field of reservoirs for liquid medicaments and in particular to reservoirs applicable for long-term storage as well as for administering a liquid medicament by means of a drug delivery device. The disclosure describes a respective drug delivery device equipped with such a reservoir.

BACKGROUND AND PRIOR ART

Drug delivery devices for administering liquid medicaments are widely known in the art. Parenteral administering of liquid medicaments is typically conducted by means of injection devices, such like syringes, pen-type injectors or by means of infusion pumps, e.g. by way of micropumps.

For treatment of chronic diseases, such like diabetes the medicament has to be regularly administered according to a predefined schedule. Known drug delivery devices may either be adapted for discrete use for injecting of a pre-defined amount of the medicament a given number of times during the day. Alternatively, such drug delivery devices may be adapted for continuous or quasi-continuous delivery of the medicament through a permanent fluid connection between the delivery device and the patient. Continuous or constant administering of the medicament is typically conducted by means of infusion pumps that are relatively expensive.

Such drug delivery devices typically comprise a reservoir to accommodate the liquid medicament and having an outlet in fluid communication with some kind of infusion or injection needle. Moreover, such drug delivery devices also comprise a drive mechanism that is operable to expel or to withdraw a predefined amount of the liquid medicament from the reservoir and through the infusion or injection needle into biological tissue of the patient.

There exist reusable as well as disposable devices, wherein with reusable devices the medicament-containing reservoir is to be replaced when empty. With disposable drug delivery devices a pre-filled reservoir is non-detachably arranged in the device. When the medicament contained therein has been used up the entire device is intended to be discarded.

Traditionally, vitreous or glass cartridges have been widely used in injection or infusion systems to contain or to accommodate the liquid medicament, hence a particular pharmaceutical composition. Glass cartridges or carpules provide a large degree of optical transparency and are substantially inert to the medicament. This means, that substantially no interaction between the medicament and the glass cartridge takes place even under long term storage conditions, i.e. when the medicament is stored and contained in the cartridge for time intervals of severely years.

Additionally, the optical transparency of the glass cartridge allows the patient to visually check the quality and integrity of the medicament. Additionally, glass provides an excellent barrier against ingress of liquid or gaseous media from the environment into the cartridge. Moreover, vitreous or glass bodies of cartridges effectively prevent leakage of the medicament from the cartridge. Therefore, vitreous cartridges or glass cartridges are widely used for long-term storage of liquid medicaments. Such cartridges pre-filled with a liquid medicament can be stored over comparatively long time intervals and may be readily assembled with or into a drug delivery device for direct delivery of the medicament from the cartridge into biological tissue of the patient.

Vitreous cartridges or glass cartridges are prone to mechanical impact and may therefore represent a concern for patients but as well for the pharmaceutical industry. Glass breakage typically represents a hazard for the patient as well as for the industrial production environment. Moreover, handling of broken glass is quite risky and dangerous for the persons concerned with a broken cartridge.

Especially with highly concentrated medicaments and with infusion pump applications comparatively small volumes have to be injected or low volume flow rates have to be realized. Extraction and withdrawal of a comparatively small amount of medicament from a vitreous cartridge may be rather elaborate since a piston typically sealing a proximal end of the cartridge is to be displaced in distal, hence in injection direction typically by means of a plunger of the drug delivery device.

Since the piston provides a proximal seal of a cartridge it is only displaceable relative to the barrel of the cartridge against static and/or dynamic friction forces. Especially with miniaturized infusion pumps that may operate in a suction mode for withdrawing the medicament from the reservoir, use of vitreous cartridges sealed with a displaceable piston are rather unsuitable. For such application scenarios use of a deformable or flexible reservoir would be advantageous.

Document US 2009/0118682 A1 describes a reservoir unit comprising a housing and a reservoir arranged at least partially within the housing. There, the reservoir comprises a first transparent area and a second area opposite the first area that comprises a visually non-uniform surface portion. The reservoir comprises first and second flexible foil portions sealed together to form an enclosed cavity for containing the fluid, wherein the reservoir has a pouch-like configuration.

Flexible and transparent foils on the basis of polymers typically do not provide a sufficient barrier against ingress or leakage of gaseous or liquid media into or from such reservoirs. Flexible and transparent pouch-like reservoirs are therefore not applicable or usable as a means for long term storage of liquid medicaments due to their poor barrier properties. Infusion pumps making use of such flexible and transparent reservoirs therefore have to be filled by the patient himself just before use of the medicament.

The insufficient barrier properties of materials that are substantially transparent and flexible impede application of these materials for long term storage of liquid medicaments. However, from a patient's point of view it would be highly desirable and practicable to make use of pre-filled reservoirs ready for use in or with a drug delivery device.

Aspects of the disclosure can be implemented to provide a reservoir for a liquid medicament which allows for visual inspection of its content, which provides sufficient mechanical strength as well as long term storage stability for the medicament contained therein. Additionally, the reservoir should provide a high barrier, both in terms of moisture and gas. Moreover, the reservoir should be less prone to mechanical impact as compared to vitreous cartridges and should further provide easy extraction of its content even with comparatively low suction forces. Furthermore, the reservoir should not only provide long term storage of the medicament but should also be suitable for drug delivery. It should therefore be compatible with drug delivery devices for medicament delivery to patients.

SUMMARY

In a first aspect a reservoir for a liquid medicament is provided. The reservoir comprises a first boundary portion and a second boundary portion, wherein first and second boundary portions form at least one cavity or several cavities to receive the medicament. Here, the first boundary portion is flexible whereas the second boundary portion is rigid. The reservoir therefore comprises a non-uniform structure with first and second boundary portions having different mechanical properties regarding stiffness, stability and/or elasticity. By combining first and second boundary portions to form a cavity for accommodating the medicament, the reservoir is flexible at least in sections and is therefore mechanically deformable.

Additionally, at least one of the first and the second boundary portions is a transparent boundary portion that is covered by an opaque cover which is at least partially detachable from the transparent boundary portion or which is detachable from the reservoir as such. In effect, either the first, flexible boundary portion is covered by the cover or the second, rather rigid boundary portion is covered by said cover. By covering the transparent boundary portion of the reservoir by means of an opaque cover, materials exhibiting comparatively poor barrier properties against gaseous or liquid media can be used to form the transparent boundary portion.

The opaque cover which is either directly attached to the transparent boundary portion or which may cover the outside facing surface of the transparent boundary portion in a distance therefrom provides an additional barrier against gaseous or liquid media. Hence, the combination of the detachable opaque cover with a transparent boundary portion fulfills the requirement in regards of a barrier against gaseous and liquid media at least as long as the cover is attached to the transparent boundary portion or to the reservoir.

In such an initial configuration the reservoir may be completely non-transparent and its content may not be visually inspectable. However, in such an initial configuration, wherein the transparent boundary portion is protected by the opaque cover, the reservoir is particularly suitable for long term storage of the medicament located therein. It is only prior to use of the reservoir, that the opaque cover is at least partially detached from the transparent boundary portion. By detaching or removing the opaque cover a user, e.g. the patient or medical staff, may visually inspect the medicament and hence the interior of the cavity.

Removing and detaching of at least a portion of the cover reveals the transparent boundary portion. But since the cover is only to be removed from the transparent boundary portion for application purpose, comparatively poor barrier properties of the transparent boundary portion may become substantially negligible since the medicament contained in the reservoir is extracted therefrom over a time interval which is comparatively short compared to the shelf life or storage period of the reservoir.

By means of the detachable cover any drawbacks of a transparent boundary portion in regard of barrier properties against ingress or escape of gaseous or liquid substances can be effectively compensated at least during storage of the reservoir. Since the opaque cover not only provides protection against electromagnetic radiation but also increases the chemical barrier function of the transparent boundary portion the reservoir qualifies for long term storage as well as for direct application with a corresponding drug delivery device. Hence, the reservoir can be designed and manufactured as a reservoir pre-filled with the medicament, such that the reservoir is ready to be used with a drug delivery device.

By making use of an opaque cover for the transparent boundary portion, said transparent boundary portion can be made of transparent material that does not need to provide excellent or sufficient barrier properties in regard of the medicament to be stored in the cavity. Additionally, since the opaque cover does not contribute to the cavity formed by first and second boundary portions the opaque cover does not have to be made of material being substantially inert to the medicament to be stored in the cavity. In this way, a large variety of combinations of materials providing sufficient barrier properties on the one hand and transparent materials on the other hand can be used to form a boundary portion of the reservoir's cavity.

In the present context, the term boundary portion denotes an arbitrary portion of the reservoir enclosing the medicament receiving cavity thereof. A boundary portion may constitute or may belong to a wall portion of the reservoir. Depending on the geometry of the reservoir the boundary portions may represent sidewall portions, bottom portions or upper portions of the reservoir. Since the reservoir is not limited to a particular geometrical structure, first and second boundary portions may also be of arbitrary shape and geometry as long as they form the medicament receiving cavity. Typically, first and second boundary portions together form a closed or confined volume that coincides with the medicament receiving cavity.

According to an embodiment the first boundary portion is formed by at least one flexible material. In this way a respective flexible boundary portion can be provided which is of particular advantage when the reservoir is to be used with an infusion pump arrangement. In this way, the liquid medicament may be easily extracted or withdrawn from the cavity by way of suction. Here, the flexible material of the first boundary portion allows reduction of the size of the cavity of the reservoir as the medicament is extracted continuously or in discrete steps from the reservoir's cavity. The material the first boundary portion is made of may be elastically or plastically deformable. Especially with a plastically deformable flexible material the reservoir would not exhibit any restoring forces that could act against a suction effect of a pump in fluid communication with the reservoir's cavity.

According to another embodiment the first boundary portion is stretchable. It is typically formed by at least one stretchable material which allows for a variation of the overall size of the first boundary portion and hence of the reservoir itself. While the medicament is extracted from the cavity the first boundary portion may stretch to reduce the cavity's volume and/or to adapt to the shape and/or geometry of the second boundary portion.

It is generally conceivable, that the reservoir is filled with the medicament to such a degree, that the first boundary portion stretches to a predefined degree. In this way, the stretchable material of the first boundary portion would be applicable to establish or to maintain a particular pressure inside the reservoir's cavity. Moreover, a stretchable first boundary portion can be arbitrarily mechanically deformed, e.g. to fit into a reservoir holder of a corresponding drug delivery device.

Additionally, a stretchable first boundary portion may also be suitable to detect an eventual leakage of the reservoir. If for some reason the reservoir should be subject to leakage, the initially stretched first boundary portion initially inducing an at least slightly raised fluid pressure will inherently serve to expel at least a portion of the liquid medicament. As a consequence, the first boundary portion would become subject to a geometric modification easily discernible by the patient or user of the reservoir.

The rigid or stiff second boundary portion provides and supports a well-defined handling of the reservoir. In particular, via the second boundary portion the reservoir may be gripped and/or assembled or coupled in or with a drug delivery device.

Apart from the choice of different materials for the first and second boundary portions, first and second boundary portions may be correspondingly or symmetrically-shaped to form the medicament receiving cavity. However, first and second boundary portions may also be asymmetrically shaped to form the cavity. Depending on the choice of materials for the first and second boundary portion, the thickness of first and second boundary portions may vary. For instance, the first boundary portion may be thinner than the second boundary portion.

Moreover, it is also conceivable, that the thickness of the first boundary portion substantially equals the thickness of the second boundary portion. In other embodiments the first and flexible boundary portion could also exhibit a thickness exceeding the thickness of the second boundary portion. Independent from this, first and/or second boundary portions may comprise a uniform or even non-uniform thickness across their cavity forming surface. Consequently, the first and/or the second boundary portion may comprise sections of different thickness or sections with varying material properties, in particular to accommodate and to correspond with demands of the corresponding drug delivery device.

According to an embodiment, the first boundary portion is transparent or translucent. Hence, it is the first and flexible boundary portion that forms the transparent boundary portion that is covered by the opaque cover. Due to the cover, the transparent first boundary portion does not necessarily have to provide sufficient barrier properties against escape or ingress of gaseous or liquid media. In effect, transparent polymers substantially inert to the liquid medicament may be used that may even exhibit comparatively poor barrier properties. An eventual ingress or leakage of gaseous or liquid media through the first and transparent boundary portion can be effectively prevented by means of the opaque cover.

According to another embodiment it is the second boundary portion which is transparent and which therefore forms the transparent boundary portion being covered by the opaque cover. It is then the rigid and second boundary portion which is transparent and which is covered by the opaque cover. With the second boundary portion being transparent the first boundary portion may be opaque or substantially non-transparent. Likewise, in embodiments wherein the first boundary portion is transparent, the second and hence rigid boundary portion may be non-transparent and hence substantially opaque.

However, it is also conceivable, that both, first and second boundary portions are transparent. In this case, at least one of the two transparent first and second boundary portions will be covered with the opaque cover. Moreover, it is even conceivable, that both, first and second transparent boundary portions are covered with the detachable opaque cover.

According to another embodiment the first boundary portion is substantially collapsible onto or into the second boundary portion. Here, at least a section of the first boundary portion is collapsible or foldable onto a section of the second boundary portion. In particular, those sections of first and second boundary portions located adjacent to each other are collapsible onto each other upon extraction and withdrawal of the medicament from the reservoir's cavity.

In a further embodiment the first boundary portion may be entirely or almost entirely collapsible onto the second boundary portion. Hence, first and second boundary portions may comprise mutually corresponding surface sections and shapes that allow for a crease-free folding or collapsing of the first boundary portion onto or into the second boundary portion. In this way the content of the cavity may be completely, hence residuelessly extracted from the reservoir. Upon collapsing the inside-facing surface of the first boundary portion typically gets in direct contact with the inside-facing surface portion of the second boundary portion. Hence, during constant or repeated extraction of the medicament from the cavity, the first boundary portion folds inwardly.

At least the second boundary portion may further confine or provide a second partition of the reservoir's cavity. The first boundary portion may then stretch across an end of said second partition or may equally form a first partition of the cavity. In this case, first and second volumetric partitions each formed by first and second boundary portions mutually complement to form the reservoir's cavity.

In alternative embodiments it is conceivable, that only the second boundary portion forms a second partition of the cavity that is closed by the first boundary portion. For instance, the second boundary portion may comprise a cylindrically or tubular-shaped bottomless barrel, wherein the bottom of said barrel is formed and provided by the first boundary portion. Depending on the overall shape, geometry and flexural behaviour of the first boundary portion, the first boundary portion may either form an outwardly bulged first partition of the cavity in an initial configuration that collapses into the hollow space of the second boundary portion upon extraction of the medicament.

Alternatively, the first boundary portion may extend across an end or interface portion of the second boundary portion facing towards the first boundary portion. In such an embodiment, the first boundary portion may comprise a sheet-like planar structure that may be stretched or sucked into the hollow space of the second boundary portion upon extraction of the medicament.

Collapsing of the first boundary portion is not only beneficial for extraction of the medicament from the reservoir but also for filling the reservoir with the medicament. Initially, even prior to filling of the reservoir, the first boundary portion can be completely collapsed or taken into the second boundary portion, such that the volume confined between oppositely located surface portions of first and second boundary portions is substantially minimized.

In embodiments, wherein the shape and geometry of first and second boundary portions mutually match and wherein the size and geometry of the first boundary portion is substantially equal to the respective size and geometry of the second boundary portion, the volume of the cavity can be almost reduced to zero prior to a filling of the reservoir with the medicament.

Introducing the medicament into the cavity, hence between substantially overlapping sections of first and second boundary portions of the reservoir then leads to a deformation of the first boundary portion thereby increasing the volume of the cavity formed by first and second boundary portions, respectively. Since the initial volume of the cavity may approach zero or some negligible value, a substantially bubble-free filling of the medicament into the cartridge can be easily provided by means of the mechanically deformable and collapsible first boundary portion.

According to a further embodiment, the cover and at least one of first and second boundary portions is substantially impervious to gasses and fluids. In this way, ingress of moisture and oxygen or other liquids or gasses into the reservoir and hence into its cavity can be effectively prevented. Typically, the barriers provided by the cover and by at least one of first and second boundary portions acts in both directions. The cover as well as at least one of first and second boundary portions are operable to prevent leakage of gaseous or liquid media from the cavity of the reservoir. Implementing a comparatively high barrier against gasses and liquids, in particular against oxygen and moisture allows to use the reservoir for long term storage of medicaments. Hence, the medicament may be stored in the reservoir for at least one year or even for more than two or three years.

According to a further embodiment the cover exhibits a larger barrier against gaseous and/or liquid substances compared to the first boundary portion or compared to the second boundary portion. Typically, the barrier properties of the cover outreach the barrier properties of the transparent boundary portion that is covered by said opaque cover. In this way, even poor barrier properties of the transparent boundary portion can be effectively compensated.

According to another embodiment the reservoir further comprises at least one outlet port in fluid connection with the cavity and intersecting at least one of first and second boundary portions. The at least one outlet port may be provided at an end of the second boundary portion facing away from the first boundary portion. In this way, the outlet port will not be clogged or blocked by the first boundary portion e.g. when collapsing into the second boundary portion during withdrawal of the medicament.

In an alternative embodiment, the outlet port is provided on or in the first boundary portion. Additionally or alternatively the outlet port may also be provided in an interface section of first and second boundary portions. In such an embodiment the outlet port intersects both, first and second boundary portions. The outlet port may be provided with a seal that is either removable or penetrable to provide access to the cavity and to the medicament provided therein. Typically, the outlet port may be sealed with some kind of elastic plug or seal, such like a septum that is penetrable by e.g. an injection needle. When provided as a plug or seal, the outlet port may be arranged in a through opening of the second boundary portion. Then, the plug or seal serves to effectively close the outlet opening of the second boundary portion.

In other embodiments, wherein the outlet port is for instance integrated into the first boundary portion, the outlet port may comprise a tube, e.g. a tube port integrally formed with the mechanically deformable or flexible material of which the first boundary portion is made of. The outlet port may further be equipped and provided with a standardized connector, such like a latch, a screw or a bayonet thread in order to attach the outlet port of the reservoir with some kind of drug delivery mechanism.

However, there may also be embodiments wherein the reservoir is designed outlet-less or free of any outlet. It is then intended, that at least one of first and second boundary portions is intersectable or piercable by some kind of extraction device, such like an extraction needle or injection needle.

According to a further embodiment, the first boundary portion and the second boundary portion are mutually connected or bonded along a circumferentially extending seam. In embodiments, wherein the second boundary portion comprises a tubular-shaped barrel or a cup-shaped receptacle, the circular end section of the second boundary portion is connected or bonded along its complete outer circumference with the first boundary portion to form the closed cavity. But also in embodiments wherein the second boundary portion comprises a substantially flat-shaped geometry or wherein the second boundary portion comprises cup-, pot- or well-like shape an upper rim of the second boundary portion is typically completely bonded or connected with the first boundary portion to form the closed cavity.

Typically, first and second boundary portions are bonded or welded in a liquid- and/or gas-tight manner. Mutual bonding or welding of first and second boundary portions should not only prevent any leakage of the medicament during storage but also upon drug delivery. The connection of first and second boundary portions should resist any pressure, tension or mechanical stress exerted on the reservoir, especially during extraction, either by suction or by applying pressure to the reservoir for expelling an amount of the medicament. First and second boundary portions can be bonded by at least one of the following methods: heat sealing, hot gas welding, hot plate welding, laser welding, friction welding, vibrational welding, ultrasonic welding, high-frequency welding, solvent welding, or by use of a glue or a tie material.

Moreover, the material's first and second boundary portions are made of should be substantially inert in regard to the medicament to be stored in the reservoir.

Filling of the reservoir typically takes place under aseptic conditions, in particular if the medicament itself is prone to degradation during sterilisation. Filling of the reservoir during manufacture of the reservoir may further help to reduce contamination and particle counts form, e.g. in form fill seal, blow fill seal, co-extrusion blow fill seal or stretch blow fill seal.

In another embodiment the cover is flexible. It may comprise a flexible foil or a laminate structure, e.g. comprising one or several layers in order to provide a sufficient barrier against gaseous and liquid substances.

In contrast to that and according to another embodiment the cover is rigid or stiff. In either way, a flexible or a stiff cover may form a kind of a secondary packaging for the reservoir which is to be detached or removed from a transparent boundary portion underneath prior usage of the reservoir.

When the cover is rigid it may further serve to provide mechanical protection for the cavity at least partially located therein. A rigid cover may be cup-shaped to form a receptacle to receive the reservoir's cavity therein. Alternatively, the cover may be planar-shaped to provide a support face for the transparent boundary portion, which in this case may be rigid or flexible. In case of a flexible transparent boundary portion, the rigid cover may act as mechanical stabilization for the transparent and flexible boundary portion. The second boundary portion, which is generally rigid, may then form a rigid encapsulation for the cavity with the rigid cover.

In another embodiment, wherein the transparent boundary portion, to which the opaque cover may be attached is rigid, hence when the cover effectively covers the second boundary portion, the cover may be flexible and may be adhered or attached to the rigid but transparent boundary portion.

Detaching of the opaque cover from the transparent boundary portion may be supported by a predefined weakening structure, e.g. by a scoring line or by a perforation. Upon detaching the cover from the transparent boundary portion the cover may remain intact or may disintegrate to reveal the transparent boundary portion of the cavity.

In general, detaching of the opaque cover from the cavity may be of reversible or irreversible type. Hence, at least a section of the opaque cover may be detached from the transparent boundary portion in such a way that after visual inspection of the cavity said detached portion of the opaque cover is re-attachable to the respective boundary portion.

According to another embodiment the cover is attached to the entire surface of the transparent boundary portion. Hence, the opaque cover may comprise a foil or a laminate structure extending all over the surface of the transparent boundary portion and being in direct surface contact with said boundary portion. Hence, the cover may comprise a protective film, a foil or a laminate that may be at least partially or in sections detached from the transparent boundary portion underneath. Here, the transparent boundary portion may be flexible or rigid and may thus represent the first boundary portion or the second boundary portion of the cavity.

In another embodiment, the cover is only punctually or in sections connected or attached to at least one of first or second boundary portions. The cover extending across the transparent boundary portion may be directly attached to said transparent boundary portion. Even though the opaque cover extends across the transparent boundary portion, e.g. across the first boundary portion it may be not in direct contact with the transparent, e.g. with the first boundary portion. Instead, the opaque cover may be connected and attached to the second boundary portion, which does not need to be transparent.

However, detaching of the opaque cover from the second boundary portion may reveal the first, hence the transparent boundary portion. Such configurations are in particular conceivable, when the transparent boundary portion is somehow encapsulated by the other, typically non-transparent boundary portion.

According to another embodiment, the cover is at least in sections peelable from the transparent boundary portion. In this embodiment, the cover typically comprises a foil or laminate structure, which may be adhered or attached to the entire or complete surface of the transparent boundary portion. Revealing of the transparent boundary portion simply requires to scratch off the cover or portions thereof. Apparently, the cover may also comprise a detachable coating on the outside of the transparent boundary portion. A coating but also a foil or a laminate has only minimal influence on the overall weight and geometry of the reservoir. Additionally, such a coating, foil or laminate may be realized rather cost efficient.

According to a further embodiment, the second boundary portion or the cover forms a receptacle that is traversed or closed by at least one of the first or second boundary portion of the cavity. Then, at least one of first or second boundary portions may effectively serve as a lid for the receptacle being formed by the cover. Here, the cover may form a mechanical support structure to receive a transparent boundary portion, e.g. the flexible and first boundary portion of the cavity while the receptacle formed by the cover is effectively closed by the second and rigid boundary portion.

In such a configuration, the second boundary portion and the rigid cover form an encapsulation for the cavity. Here, the transparent and flexible boundary portion of the cavity may be completely enclosed by the cover. An open end of the cover, e.g. a circumferential rim thereof may be releasably connected with the rigid second boundary portion. Detaching of the cover from the cavity therefore resembles extracting and removing the cavity from a secondary packaging formed by the receptacle-shaped cover.

When the second boundary portion forms the receptacle, e.g. of cup-like shape, its opening may be covered or traversed by the first boundary portion, e.g. in combination with the cover. When the cover forms the receptacle, it may be covered or traversed by the second boundary portion or by the first boundary portion.

In still another embodiment the transparent boundary portion is dyed. In this way, the respective boundary portion may provide a spectral filter for selected wavelength of the electromagnetic spectrum. Having a transparent but dyed boundary portion the liquid medicament provided in the cavity of the reservoir can be effectively protected against electromagnetic radiation of selected wavelengths that may deteriorate or harm the medicament located in the cavity.

According to a further embodiment, the second and rigid boundary portion comprises at least one of a glass or a vitreous material, a rigid and transparent polymeric material or a combination thereof. Hence, the second boundary portion may comprise a vitreous section and a rigid and transparent polymeric section. Typically, at least one or a combination of the following polymeric materials may be used for the second boundary portion: polyethylene (PE), in particular low-density polyethylene (LDPE), linear low-density polyethylene (LLDPE), medium-density polyethylene (MDPE), polypropylene (PP), in particular in form of a homopolymer, random or heterophasic copolymer, cyclic olefin copolymer (COC), cyclic olefin polymers (COP), polymethylene pentane, polyethylene terephthalate (PET), polybutylene terephthalate (PBT), polycarbonates (PC), polystyrene (PS), styrene acrylonitrile resin (SAN), methyl methacrylate-acrylonitrile-butadiene-styrene-polymer (MABS), polyvinyl chloride (PVC).

According to another embodiment, the first boundary portion comprises at least one of an elastomeric material, a flexible thermoplastic material, a layer of polymeric material or combinations, composites and laminates thereof.

In particular, the first boundary portion may comprise at least one of the following materials: thermoplastic elastomers (TPE), silicon rubber, butadiene rubber (BR), styrene butadiene rubber (SBR), styrene-ethylene/butylene-styrene type polymers (SEBS), LDPE, LLDPE, ethylene vinyl acetate (EVA), random copolymers of VP, polybutene-1, COC- or COP-based elastomers.

In particular when the first boundary portion comprises a comparatively thin layer of polymeric material, one of the following materials or combinations thereof can be used to form the first boundary portion: MDPE, high-density polyethylene (HDPE), PP, in form of homopolymer, random or heterophasic copolymers, polybutene-1, COC, COP, polymethylene pentane, PET, Polyethylenterephthalat Glycol (PET-G), PBT, PC, SAN or MABS. In general, the first boundary portion may comprise at least one or a combination of the above mentioned materials.

According to another embodiment, the first boundary portion and/or the cover comprises a multilayer structure. Hence, the first boundary portion comprises at least two substantially overlapping layers of different materials. Here, a combination of comparatively thin layers or foils of even rigid materials, such like MDPE, HDPE, PP, polybutene-1, COC, COP, polymethylene pentane, PET, PET-G, PBT, PC, PS, SAN, MABS and arbitrary combinations thereof can be used to form the first boundary portion and/or the cover. Especially when comprising a multilayer structure, the first boundary portion and/or the cover may also comprise at least one layer of polychlorotrifluoroethylene (PCTFE), polyamide (PA), ethylene-vinyl alcohol (EVOH) or polyparylene that can be used as barrier layer in a multilayer structure.

The barrier properties of said materials can be further improved by the use of passive barrier additives, such as polymer platelets of e.g. PA or EVOH, inorganic fillers, such as $SiO_2$, talc, and/or nanocomposites, such like nanoclays. Moreover, also active barrier additives, such as molecular sieves or chemical reactants, including oxidizable compounds may help to reduce the ingress of gaseous or liquid substances. Alternatively or in addition, coatings or laminates are generally applicable to improve the barrier properties of the cover.

According to a further embodiment, the cover may therefore comprise at least one metal foil, typically an opaque metal foil. In effect, the cover may be laminated with a metal foil or may be even metallized, e.g. with aluminum, metal oxides or metal nitrides, that may be summarized as $MO_wN_xC_yH_z$, wherein M represents a single or a combination of metals. In this way, the first boundary portion may comprise a foil or a layer of $SiO_x$, $SiO_xC_yH_z$, $SiO_xN_y$, $SiN_x$, $AlO_x$, $TiO_x$.

Making use of a metal layer, e.g. in form of a metal foil or a metallic coating, the barrier properties of the cover may be further improved. Additionally, use of metal foils may provide a cost efficient approach to manufacture such reservoirs.

According to another embodiment, the first boundary portion and/or the cover at least in sections is laminated or coated. Typically, the complete first boundary portion is laminated or coated, either with a metallic coating or with an inorganic coating. Typically, the coating may comprise carbon, metal oxides or metal nitrides, partly with organic components, that can be summarised as $MO_wN_xC_yH_z$, in which M represents a single or a combination of metals. Additionally or alternatively also organic coatings, such like polyparylene, epoxy or epoxy amine resins can be used here. Moreover or alternative, the outer or inner surface of the first boundary portion and/or of the cover may be chemically modified. Here, a chemical surface modification, such as fluorination of polymers can be used to improve the barrier properties of the first boundary portion.

Production of the first boundary portion, of the second boundary portion and/or of the cover may be conducted separately. The first and hence flexible boundary portion may be manufactured by way of extrusion, extrusion blowing or casting while production of the second and rigid boundary portion may include at least one of the following production processes: extrusion, extrusion blow molding, injection blow molding, injection molding, compression molding or thermal forming. Additionally and optionally manufacturing processes comprising an orientation step such as in the production of blown, double bubble or bi-oriented film or in stretch blow molding of hollow articles may be further helpful to improve transparency and barrier properties in addition to the mechanical properties of the second boundary portion.

Depending on whether the cover is flexible or stiff it may be manufactured in a way similar to the first or to the second boundary portion. In particular, when the cover is of flexible type, it may also be formed by lamination or as a coating.

According to another embodiment, the cavity of the reservoir is at least partially filled with the liquid medicament. In particular, the reservoir is pre-filled with the liquid medicament. Moreover and when designed as a reservoir to be coupled with an infusion pump, the reservoir may comprise a comparatively small cavity volume of less than 10 ml, less than 5 ml or less than 3 ml.

By having first and second boundary portions separately providing visual inspection of the content of the reservoir and supporting and allowing a mechanical deformation thereof during medicament extraction, the reservoir can be manufactured by making use of materials being long-term tested in the pharmaceutical environment. This allows to manufacture pre-filled reservoirs that are applicable for long-term storage as well as for immediate application with drug delivery devices, such like infusion pumps or pen-type injectors.

According to another aspect the disclosure also describes a drug delivery device for dispensing of a liquid medicament. The drug delivery device is typically adapted to receive and/or to engage with the reservoir to extract or to expel a predefined amount of the medicament therefrom. The drug delivery device is typically designed as an injection or infusion device. It may be operable to apply a pressure to the reservoir for expelling the medicament or it may be operable to withdraw the liquid medicament from the reservoir in a suction mode. The drug delivery device may comprise a pen-type injector or an infusion pump.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present disclosure without departing from the spirit and scope of the disclosure. Further, it is to be noted, that any reference signs used in the appended claims are not to be construed as limiting the scope of the present disclosure.

BRIEF DESCRIPTION OF THE DRAWINGS

In the following, various embodiments of the disclosure will be described by making reference to the drawings, in which.

DETAILED DESCRIPTION

Figure 1:
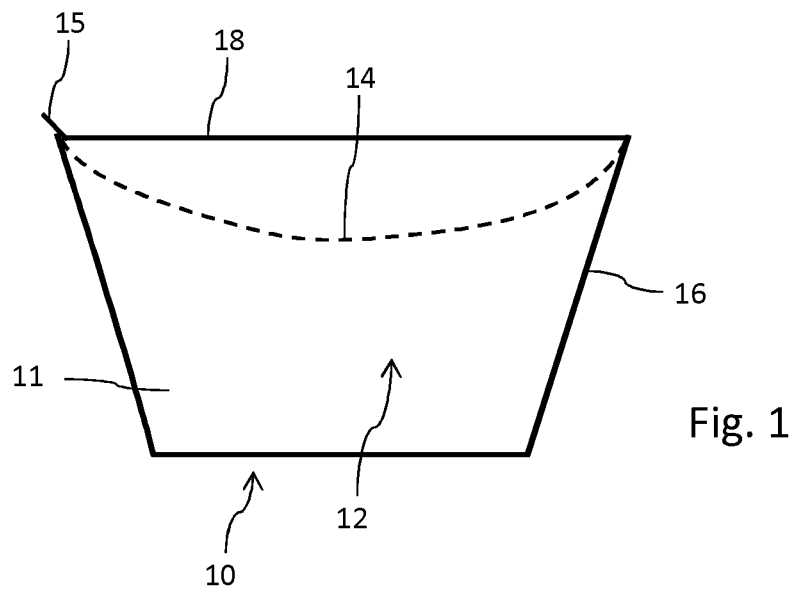
FIG. 1 schematically shows an initial configuration of a reservoir according to a first embodiment.

In FIG. 1, a reservoir 10 is schematically illustrated that comprises a cup-shaped second and rigid boundary portion 16 forming a closed cavity 12 with a first boundary portion 14. The first boundary portion 14 is flexible and may be subject to mechanical deformation in the course of extracting the medicament 11 from the cavity 12. The second boundary portion 16 is of cup-like shape and comprises a substantially planar-shaped bottom section with upwardly and radially outwardly extending sidewalls or with a single substantially conically-shaped sidewall. Near the upper end of the sidewall of the second boundary portion 16 the first boundary portion 14 extends all over the interior diameter of the cup-shaped second boundary portion 16 thereby forming the closed cavity 12 to accommodate the liquid medicament 11.

Additionally, the reservoir 10 is further equipped with an opaque cover 18 which extends across the first boundary portion 14. The first boundary portion 14 is substantially transparent and allows for visual inspection of the medicament 11 contained in the cavity 12. Consequently, the rigid and second boundary portion 16 may be also transparent but does not have to be transparent. The flexible and transparent first boundary portion 14 may comprise comparatively poor barrier properties against liquid or gaseous substances, such like water vapour and oxygen.

In order to compensate the comparatively poor barrier properties of the first boundary portion 14, the opaque cover 18 extends all over the first boundary portion 14 even at a particular distance. Here, the outer edges or an outer rim of the cover 18 may be releasably or detachably connected to the second boundary portion 16 and/or to the first boundary portion 14. The cover 18 may either be rigid or flexible. In case of a flexible cover 18, it may be peeled off or simply taken away with the help of a gripping tab 15 extending from the outer circumference of the cover 18.

Figure 2:
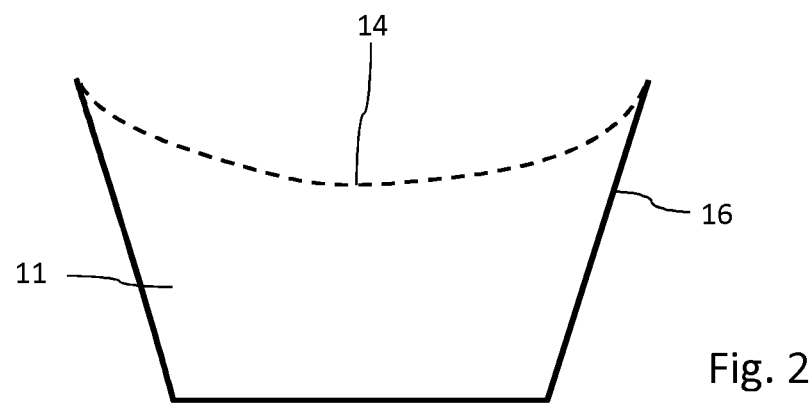
FIG. 2 shows the reservoir according to FIG. 1 after removal of the opaque cover.

The cavity 12 formed by first and second boundary portions 14, 16 as illustrated in FIG. 2 may comprise some kind of outlet port, which is not particularly illustrated here. The outlet port may either penetrate the first or the second boundary portion 14, 16 in order to provide access to the cavity 12 and hence to the medicament 11 accommodated therein. The flexibility or the flexural behaviour of the first boundary portion 14 is of particular benefit during extraction of the medicament 11 from the cavity 12.

Moreover, the first boundary portion 14 may be stretchable and may comprise at least one stretchable material, which allows that the first boundary portion 14 substantially collapses into the second boundary portion 16 upon withdrawal or extraction of the medicament 11 from the cavity 12. In this way, the medicament 11 may be residuallessly extracted from the cavity 12.

In embodiments, wherein the cover 18 is substantially rigid, the second boundary portion 16 and the cover 18 form a rigid encapsulation for the cavity 12. Here, the cover 18 may further serve as a kind of a secondary packaging, wherein the second boundary portion 16 forms part of both, the secondary packaging and of a primary packaging, the latter of which being provided by the cavity 12 and being in direct contact with the medicament 11.

Figure 3:
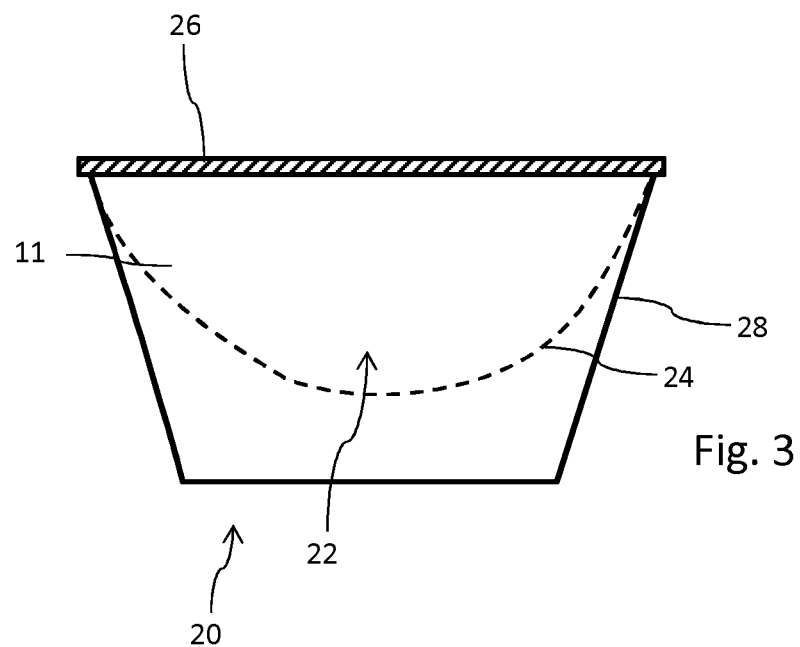
FIG. 3 shows another embodiment of a reservoir in an initial configuration.
Figure 4:
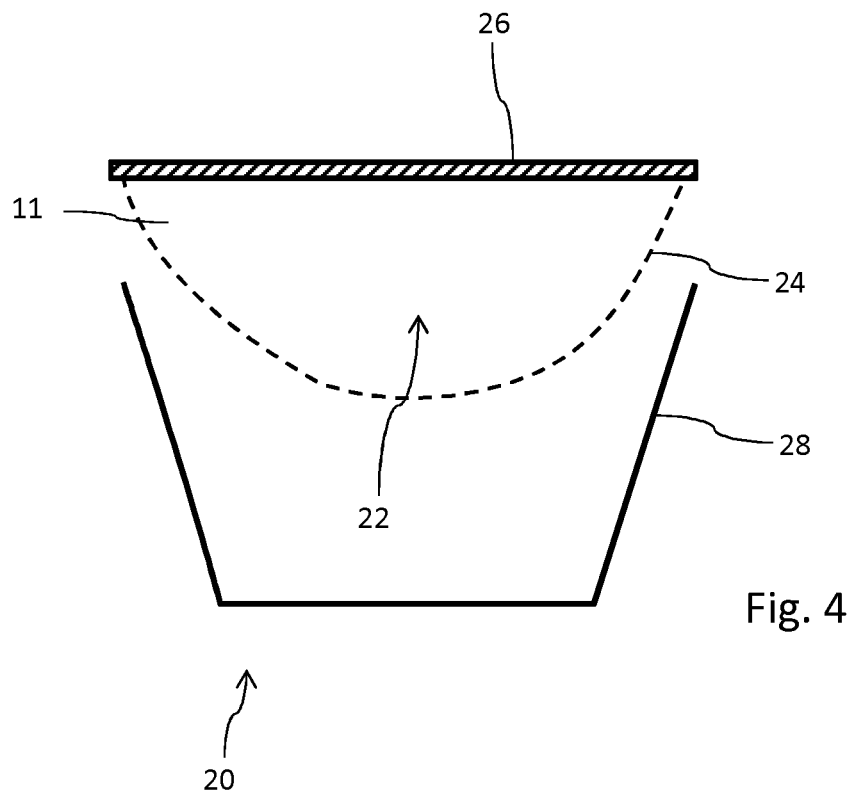
FIG. 4 shows the reservoir according to FIG. 3 with detached cover, FIG. 5 schematically shows a blister type embodiment of the reservoir in an initial configuration.

In the embodiment according to FIGS. 3 and 4 the reservoir 20 comprises a cavity 22 formed of a substantially planar-shaped second and rigid boundary portion 26 and by a flexible first boundary portion 24. In this embodiment also a substantially rigid encapsulation for the cavity 22 is provided. Here, the cover 28 is of cup-like shape and may resemble the second boundary portion 16 in the embodiment according to FIGS. 1 and 2. However, in the embodiment according to FIGS. 3 and 4, the cover 28 forms a receptacle to receive the first boundary portion 24 while the receptacle and in particular its upper through opening is effectively closed by the rigid second boundary portion 26.

Even though the cover 28 extends all over the first, flexible and transparent boundary portion 24 it may not be in direct contact or in direct connection with the first boundary portion 24. Instead, the stiff or substantially rigid cover 28 may be exclusively connected and attached to a circumferential portion of the planar-shaped second boundary portion 26.

Upon detaching the cover 28 from the second boundary portion 26, the cavity 22 may be taken out of the receptacle-forming cover 28. Thereafter, the content of the cavity 22, hence the medicament 11, may be visually inspected by medical staff or by the patient himself through the transparent first and flexible boundary portion 24 before the cavity 22 is engaged or coupled with a drug delivery device for administering of the medicament 11, typically, by way of injection or infusion.

As becomes apparent from FIGS. 3 and 4, the cup-shaped cover 28 forms a kind of a rigid tray that serves to protect the cavity 22 against moisture, ingress or escape of gasses and which further provides mechanical protection.

Figure 5:
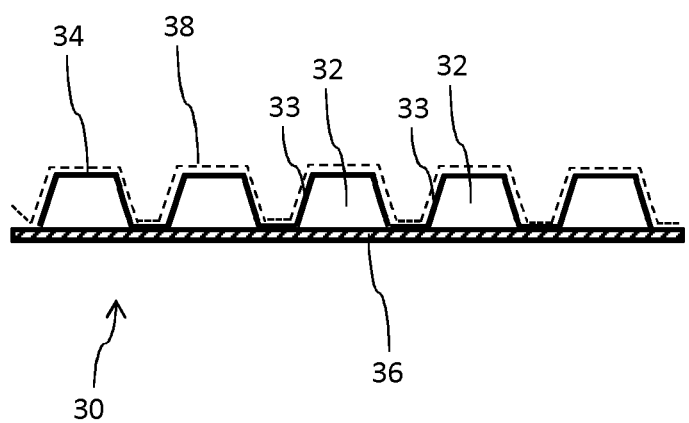

In FIG. 5, another embodiment of a reservoir 30 is illustrated. Here, the reservoir 30 comprises several cavities 32 that are formed by a first and flexible boundary portion 34 featuring a variety of recesses 33 or wells that are closed and covered by a substantially planar-shaped second and rigid boundary portion 36. Here, the second boundary portion 36 provides mechanical support for the reservoir 30.

In general, the assembly of first and second boundary portions 34, 36 forming a multiplicity of cavities 32 generally resembles a blister type packaging, wherein the various cavities 32 formed by the recesses 33 of the first boundary portion are directly filled with a liquid medicament. Here, the first boundary portion 34 may comprise a one or two-dimensional well plate sealed and covered by the second boundary portion 36.

Also here, the first boundary portion 34 is transparent and allows for visual inspection of the cavities 32 and the medicament 11 located therein. Since the first boundary portion 34 is flexible and transparent it may only provide insufficient barrier properties against liquid and gaseous substances. For this purpose, the upper surface of the first boundary portion 34 that faces away from the second boundary portion 36 is completely and directly covered by a cover 38. The cover 38 may be peelable or scratched off from the first boundary portion 34 just before use of the reservoir 30 or just before use of single cavities 32 thereof. Similar and as already explained above, the cover 38 provides a sufficient barrier against ingress or escape of liquid or gaseous substances into or from the various cavities 32.

The cover 38 may comprise a flexible foil or a coating adhered to the outside facing surface of the first boundary portion 34. Alternatively, the cover 38 may also be rigid and may provide mechanical stability to the first boundary portion 34 and to its various recesses 33.

Figure 6:
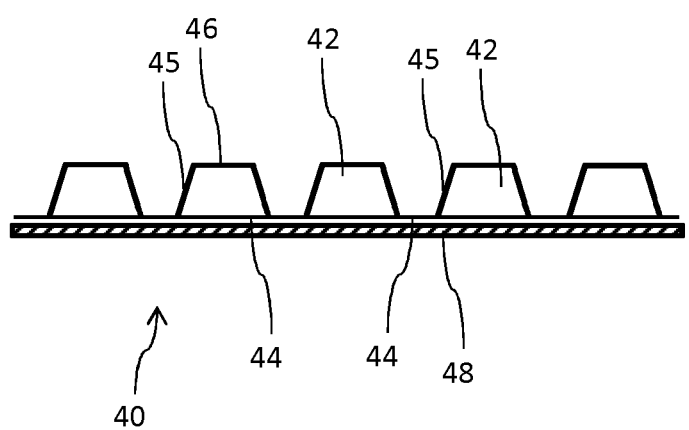
FIG. 6 shows another embodiment of a reservoir with several cavities, FIG. 7 schematically shows another embodiment of a reservoir in an initial configuration

In the embodiment according to FIG. 6, the reservoir 40 also comprises a plurality of cavities 42, each of which formed by a flexible but planar-shaped first boundary portion 44 and by a second boundary portion 46 featuring a one or two-dimensional array of recesses 45. Here and in contrast to the configuration according to FIG. 5, the cover 48 is also planar-shaped and extends all over the outer surface of the first boundary portion 44 that faces away from the second boundary portion 46. The reservoir 40 may again resemble a blister type packaging with a plurality of medicament-containing cavities 42.

Typically, the planar-shaped cover 48 is substantially rigid and non-flexible. It may only be occasionally attached to the first boundary portion 44 in order to support a rather easy and well-defined detachment thereof. Also here, the cover 48 and the second boundary portion 46 form a substantially rigid encapsulation for the various cavities 42. However, it is generally conceivable, that the cover 48 is also flexible. Between adjacent recesses 45, first and second boundary portions 44, 46 may substantially overlap. However, it is also conceivable, that only the first boundary portion 44 or the second boundary portion 46 extends between neighbouring recesses 45.

Figure 7:
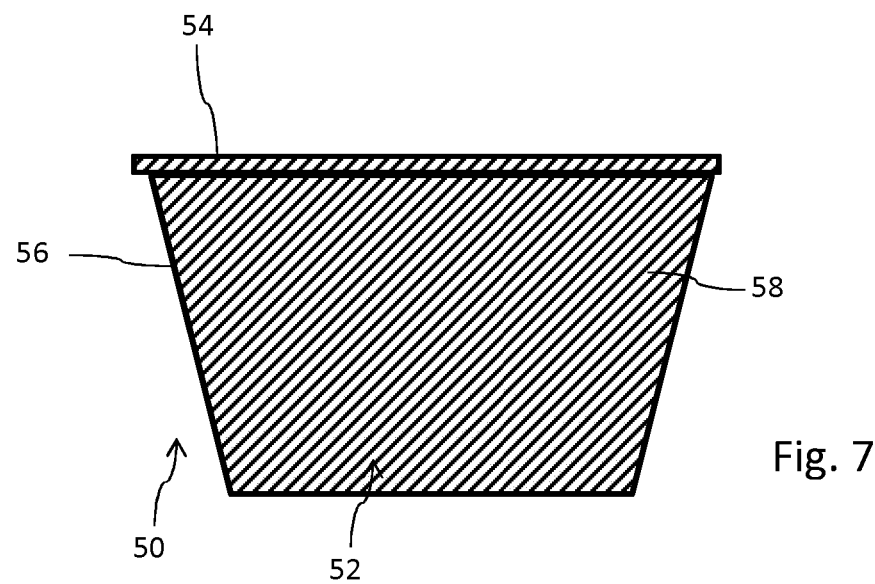
Figure 8:
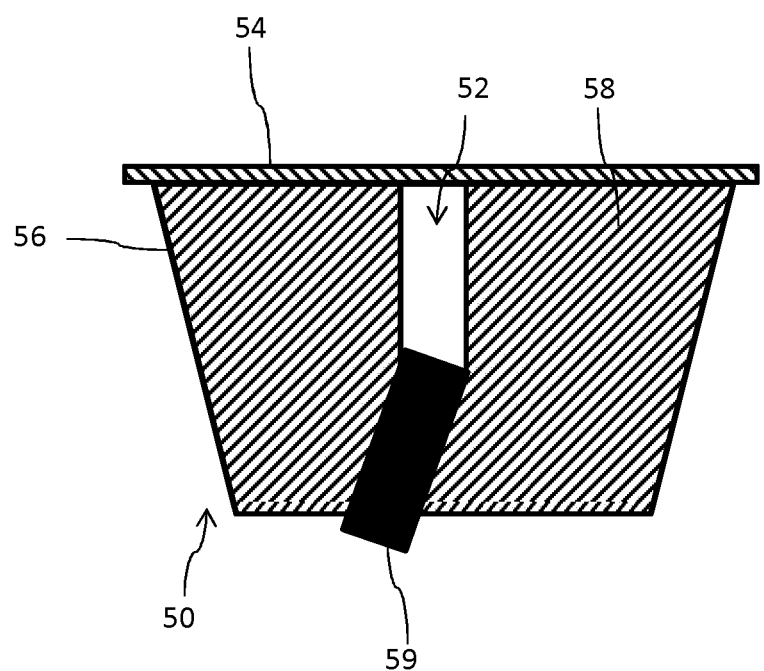
FIG. 8 shows the reservoir according to FIG. 7 after detaching of a portion of the cover.

In the embodiment according to FIGS. 7 and 8 the reservoir 50 comprises a cavity 52 which is formed by a planar and flexible first boundary portion 54, which effectively closes or seals a substantially rigid and cup-shaped second boundary portion 56. Here, the second boundary portion 56 is transparent and is further covered with a detachable cover 58. As indicated in FIG. 8, the cover 58 may be at least in sections peeled off or scratched off from the second boundary portion 56. As illustrated in FIG. 8, a flap 59 has been peeled off to reveal the cavity 52 formed by first and second boundary portions 54, 56.

Here, the second boundary portion 56 forms a cup-shaped receptacle substantially closed and sealed by the flexible first boundary portion 54. Here, the first and flexible boundary portion 54 may be substantially opaque while the rigid second boundary portion 56 is substantially transparent in order to allow visual inspection of the cavity 52 after an at least partial removal of the cover 58. The cover itself may be flexible, such like foil.

However, it may be also comparatively rigid and may thus disintegrate or crack upon removal from the second boundary portion 56.

LIST OF REFERENCE NUMERALS 10 reservoir
11 medicament
12 cavity
14 first boundary portion
15 gripping tab
16 second boundary portion
18 cover
20 reservoir
22 cavity
24 first boundary portion
26 second boundary portion
28 cover
30 reservoir
32 cavity
33 recess
34 first boundary portion
36 second boundary portion
38 cover
40 reservoir
42 cavity
44 first boundary portion
45 recess
46 second boundary portion
48 cover
50 reservoir
52 cavity
54 first boundary portion
56 second boundary portion
58 cover
59 flap

The invention claimed is:

1. A reservoir for a liquid medicament, the reservoir comprising:
    a first boundary portion; and
    a second boundary portion,
    wherein the first boundary portion and the second boundary portion form at least one closed cavity to receive the liquid medicament, wherein the first boundary portion is flexible, wherein the first boundary portion and the second boundary portion are connected or bonded to each other along a circumferentially extending seam, wherein the second boundary portion is rigid, and wherein at least one of the first boundary portion or the second boundary portion is a transparent boundary portion covered by an opaque cover which is at least partially detachable from the transparent boundary portion, wherein the opaque cover comprises a foil, a laminate structure, or a coating, wherein the foil, the laminate structure, or the coating extends over an entire surface of the transparent boundary portion of the at least one of the first boundary portion or the second boundary portion and is adhered to an outside facing surface of the transparent boundary portion of the at least one of the first boundary portion or the second boundary portion.

2. The reservoir according to claim 1, wherein the first boundary portion is stretchable.

3. The reservoir according to claim 1, wherein the first boundary portion is transparent.

4. The reservoir according to claim 1, wherein the second boundary portion is transparent.

5. The reservoir according to claim 1, wherein the first boundary portion is collapsible onto or into the second boundary portion.

6. The reservoir according to claim 1, wherein the opaque cover and the at least one of the first or second boundary portions is impervious to gases and fluids.

7. The reservoir according to claim 1, wherein the opaque cover exhibits a larger barrier against gaseous or liquid substances compared to the first boundary portion or compared to the second boundary portion.

8. The reservoir according to claim 1, wherein the opaque cover is flexible.

9. The reservoir according to claim 1, wherein the opaque cover is rigid.

10. The reservoir according to claim 1, wherein the opaque cover comprises a plurality of sections, each section being peelable from the transparent boundary portion.

11. The reservoir according to claim 1, wherein the second boundary portion or the opaque cover forms a receptacle traversed or closed by the first boundary portion or wherein a receptacle formed by the opaque cover is traversed or closed by the second boundary portion.

12. The reservoir according to claim 1, wherein the first boundary portion comprises at least one of an elastomeric material, a flexible thermoplastic material, a layer of polymeric material, or combinations, composites or laminates thereof.

13. The reservoir according to claim 1, wherein the at least one closed cavity is at least partially filled with the liquid medicament.

14. A drug delivery device for dispensing of a liquid medicament, the drug delivery device comprising:
    at least one reservoir comprising:
    a first boundary portion; and
    a second boundary portion,
    wherein the first boundary portion and the second boundary portion form at least one closed cavity to receive the liquid medicament, wherein the first boundary portion is flexible, wherein the first boundary portion and the second boundary portion are connected or bonded to each other along a circumferentially extending seam, wherein the second boundary portion is rigid, wherein at least one of the first boundary portion or the second boundary portion is a transparent boundary portion covered by an opaque cover which is at least partially detachable from the transparent boundary portion, wherein the opaque cover comprises a foil, a laminate structure, or a coating, wherein the foil, the laminate structure, or the coating extends over an entire surface of the transparent boundary portion of the at least one of the first boundary portion or the second boundary portion and is adhered to an outside facing surface of the transparent boundary portion of the at least one of the first boundary portion or the second boundary portion.

15. The drug delivery device of claim 14, wherein the liquid medicament comprises a pharmaceutically active compound.

16. The reservoir of claim 1, wherein the opaque cover is connected or attached to at least one of the first boundary portion and the second boundary portion.

17. The reservoir of claim 1, wherein the opaque cover adjoins or covers the circumferentially extending seam.

18. The reservoir of claim 1, wherein the first boundary portion and the second boundary portion form a multiplicity of cavities.

19. The reservoir of claim 18, wherein an assembly of the first boundary portion and the second boundary portion constitutes a blister type packaging.

20. The reservoir of claim 1, wherein the first boundary portion comprises a one or two-dimensional well plate sealed and covered by the second boundary portion.

21. The reservoir of claim 1, wherein the opaque cover comprises a gripping tab extending from an outer circumference of the opaque cover.

* * * * *